United States Patent [19]

Kremer et al.

[11] 4,272,381
[45] Jun. 9, 1981

[54] THIN-LAYER CHROMATOGRAPHY SPOTTING

[75] Inventors: Richard D. Kremer, Keene, N.H.; Michael J. Siebengartner, Del Mar, Calif.

[73] Assignee: Schleicher & Schuell, Inc., Keene, N.H.

[21] Appl. No.: 87,074

[22] Filed: Oct. 22, 1979

[51] Int. Cl.³ .............................................. B01B 15/08
[52] U.S. Cl. ................................ 210/658; 210/198.3; 422/70
[58] Field of Search ......................... 210/31 C, 198 C; 422/70

[56] References Cited

U.S. PATENT DOCUMENTS

| | | | |
|---|---|---|---|
| 3,928,203 | 12/1975 | Kremer | 210/198 C |
| 4,126,554 | 11/1978 | Rainin | 210/198 C |
| 4,139,458 | 2/1979 | Harrison | 210/198 C |

*Primary Examiner*—John Adee
*Attorney, Agent, or Firm*—William R. Hulbert

[57] ABSTRACT

A device for spotting samples at spaced locations on the adsorbent surface of a TLC (thin-layer chromatography) plate has a base with an elevated, flat TLC plate supporting area and an adjacent stepped down solvent trough containing area separated by a step. A wicking plate, having a number of wick-holding wells, is adapted to be positioned over the trough with the wicks dipping in the trough and the upper ends of the wicks adapted to engage the adsorbent surface of a TLC plate lowered against them. A novel wick of porous polyethylene may be pre-loaded with sample and dried before being loaded into the wicking plate. The base has spaced extensions defining a cut-out over which the wicking plate can be laid for loading, being appropriately positioned by pins extending from one of its long sides engaging the step on the base. When reversed, the non-pin-containing long side of the wicking plate engages the step and positions it over the trough. The invention includes the novel method of spotting a TLC plate employing the new device.

11 Claims, 9 Drawing Figures

U.S. Patent    Jun. 9, 1981    4,272,381
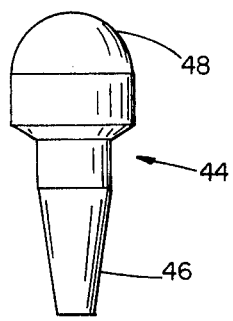
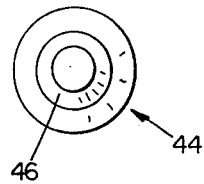
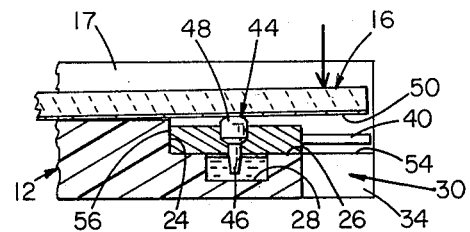
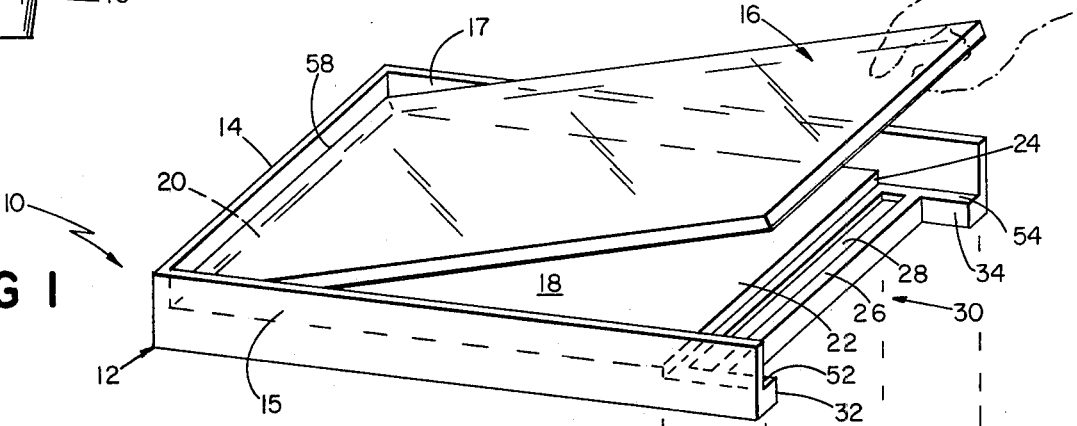
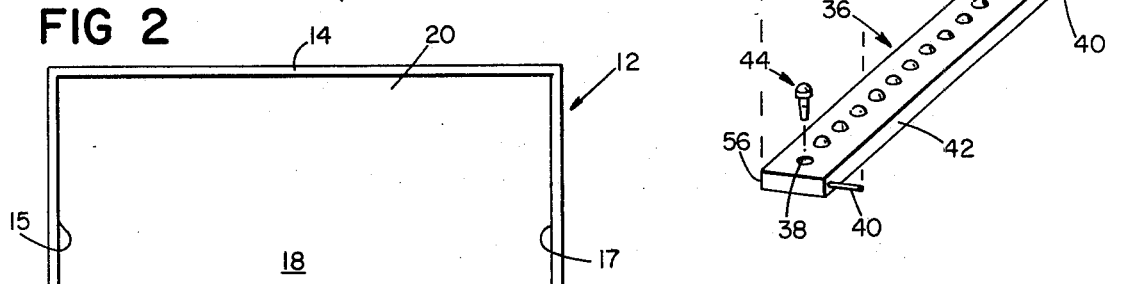
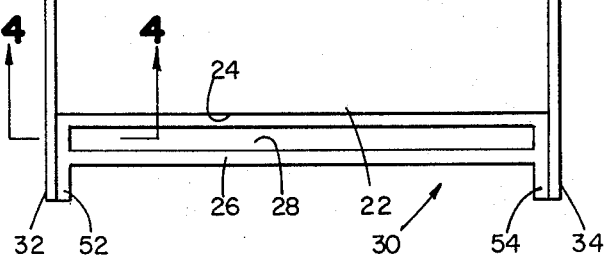
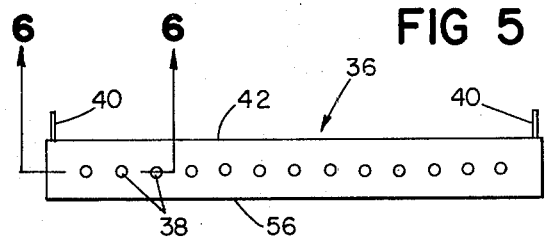
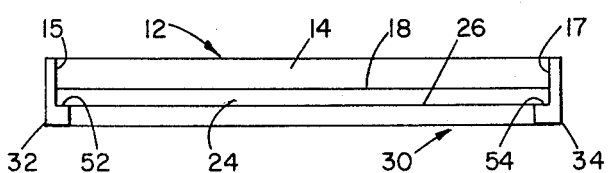
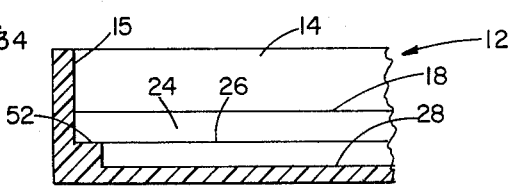

THIN-LAYER CHROMATOGRAPHY SPOTTING

BACKGROUND OF THE INVENTION

At the present time almost all sample application, spotting on TLC (thin-layer chromatography) plates is done by means of micro capillary pipets, either by hand or arranged in series in a mechanical device, to increase the efficiency and ease of the spotting operation.

The samples held and delivered by a micro capillary pipet are liquids in which the sample is dissolved and must, for analytical purposes, be generally delivered in quantities of 1 to 2 $\mu$l at a time, to keep the area of sample application (spot) small and the sample itself as concentrated as possible. In more elaborate micro capillary spotters a stream of warm air will continuously pass over the area of sample application, or that area will be warmed by an electric heating block, to speed up evaporation of the carrier liquid and dry the samples so that the spotting operation can be speeded up or sample delivery can be made on a continuous basis from micro capillaries with access to a sample reservoir. These latter devices also contain a more complex plumbing arrangement.

For concentrated samples of a few $\mu$l, hand spotting with a micro capillary pipet is probably the easiest, most cost efficient and rapid method available. However, as the sample size increases to the 20 to 50 $\mu$l range, commonly encountered in drug analysis, and large numbers of such samples must be spotted on a day to day basis, hand spotting becomes a very tedious, lengthy and laborious task. It also demands a great deal of precision on the part of the operator to apply successive increments of a sample to the same location on a plate so as to keep the spot size small. The capillary spotting devices reduce the amount of hand labor and the need for precision on the part of the operator, but still require a great deal of set up time and maintenance to replace the capillaries, fill and clean sample reservoirs, purge and clean plumbing, etc. In addition, these capillary spotters are generally fairly expensive and some of the components such as the glass capillaries, reservoirs, and plumbing are quite fragile and subject to breakage.

SHORT STATEMENT OF THE INVENTION

The spotter we have designed is meant to be used where such large sample volumes are employed and where a large number of samples must be spotted on a daily basis, such as in the mass screening programs for the detection of drugs of abuse. It is designed to overcome the weaknesses that are inherent in capillary spotting, such as (1) limited sample capacity of the capillary which can only be overcome by the use of an auxiliary sample reservoir; (2) use of fragile or delicate components, i.e., glass and plumbing; (3) use of a hard, small diameter sample applicator (the capillary pipet) which can damage the soft adsorbent surface of a TLC plate, thereby causing distortion in the pattern of the separated components when the TLC plate is developed; (4) complex construction and moving parts; (5) dependence on a large amount of precise and repetitive hand labor; (6) dependence on inherent skill and/or training.

In accordance with the invention we provide a device for spotting samples at spaced locations on the adsorbent surface of a TLC plate comprising a base member having an elevated flat TLC plate-supporting portion extending forwardly from its back and a stepped-down portion at its front containing a solvent trough and a wicking plate containing wick-receiving apertures adapted to be positioned on the stepped-down portion with the apertures over the trough so that the lower ends of wicks held in the apertures will dip in the trough, the stepped-down portion and wicking plate being so disposed and arranged that a TLC plate positioned on the elevated portion will overhand the wicking plate so as to engage and be spotted by the upper ends of the wicks. The invention also features the provision of: guides on the base adjacent the elevated portion to aid in positioning the TLC plate; a pair of spaced extensions from one of the edges of the base adapted temporarily to support the wicking plate when wicks are being loaded into the apertures, the extensions preferably extending forwardly from the base to define a U-shaped cut-out therein adjacent to the stepped-down trough-containing portion; an abutment between the elevated portion and the stepped-down portion adapted to cooperate with the wicking plate so as to position it over the trough with the lower ends of its wicks dipped therein; and spacing means along one edge of the wicking plate adapted to engage the abutment to aid in positioning the wicking plate with its apertures over the U-shaped cut-out, the other edge of the wicking plate being adapted to engage the abutment when the wicking plate is reversed to aid in positioning it with its apertures over the trough. In preferred embodiments, the base member is unitary and formed from solvent-resistant plastic and the guides comprise upstanding rails on the back and two sides thereof, and the spacing means comprises mutually spaced pins extending outwardly from one edge of the wicking plate.

The invention is further featured by the provision of a novel wick for use in a device for spotting samples at spaced locations on the adsorbent surface of a TLC plate by means of a wicking plate having apertures to receive and hold a number of wicks with their lower ends dipped in a solvent trough and their upper ends arranged to be engaged by the adsorbent surface of the plate, the wick comprising a molded chemically inert porous member adapted to absorb the sample, preferably of porous polyethylene, in a liquid solution, be dried and then inserted in an aperture in the wicking plate, the wick having a slender stem comprising its lower end portion adapted to protrude through the bottom of the aperture and contact the solvent and a bulbous dome-like upper end adapted to spot the sample non-injuriously on the adsorbent surface of the TLC plate when brought into contact with it.

The invention also includes a novel method of spotting samples at spaced locations on a TLC plate whch comprises: allowing each sample in liquid solution to be absorbed by a porous wick; drying the wick; inserting the dried wick in an aperture in a wicking plate with its upper end protruding above the upper surface of the plate and its lower end depending beneath the bottom surface of the plate; contacting the lower end of the wick with a suitable solvent to concentrate the sample in the upper end of the wick; and, bringing such upper end into contact with the adsorbent surface of the TLC plate to spot the sample on such surface. The sample may be concentrated in the upper end of the wick by dipping the lower end in the solvent or by touching the base of the wick stem with a strip of absorbent material saturated with the solvent, or both.

BRIEF DESCRIPTION OF THE DRAWINGS

In the drawings,

FIG. 1 is a view in perspective of the novel device showing a wicking plate removed from its position over the solvent trough and a TLC plate about to be lowered into contact with the wicks so as to be spotted with samples contained in the wicks;

FIG. 1A is a fragmentary cross-section showing a portion of the wicking plate positioned so that the upper ends of the wicks engage the adsorbent surface of the TLC plate and the stems of the wicks dip in the solvent trough;

FIG. 2 is a plan view of the base itself;

FIG. 3 is a front elevation thereof;

FIG. 4 is a fragmentary cross-section taken on line 4—4 of FIG. 2;

FIG. 5 is a plan view of the wicking plate itself;

FIG. 6 is a fragmentary cross-section taken on line 6—6 of FIG. 5;

FIG. 7 is a front elevation on a greatly enlarged scale of one of the novel wicks employed in carrying out the invention; and FIG. 8 is a bottom view of the same.

DETAILED DESCRIPTION OF PREFERRED EMBODIMENT

The device we have invented consists of three components. These are:

Spotter Base—The base unit 10 is fabricated preferably from polypropylene or Delrin, materials having good resistance to organic solvents. The body 12 of the spotter base 10 is enclosed on three sides by integral guide rails 14, 15, 17 which serve to hold, guide and prevent any excessive shifting movement of the TLC plate 16 during the spotting operation. The base body consists of an elevated broad, flat portion 18 toward the enclosed end 20 of the unit, on which the TLC plate 16 can be laid. At the open end 22 of the unit 10, a step 24 defining an abutment has been cut below the level of the broad plate holding area. The stepped-down portion 26 contains a solvent trough 28, to hold the transfer solvent during the spotting operation and a wide, U-shaped cut-out 30, over which the wicking plate can be placed during the wick loading operation, and which is defined by extensions 32, 34 of the body 12 of the base 10.

Wicking Plate—The wicking plate 36 is preferably fabricated from stainless steel and contains a series of uniformly spaced apertures or wells 38, which extend all the way through, for the placement of the wicks. In the drawing the wicking plate is shown with thirteen such wells. In actual practice any desired number of wells, up to a practical maximum of nineteen, can be accommodated in the wicking plate.

Two steel pins 40 are inset into the long edge 42 of the wicking plate 36 farthest from the wells. These pins serve as stops engaging step 24, when the wicking plate is laid on the extensions 32, 34, with its pins 40 facing the abutment 24, to properly position the plate over the U-shaped cut-out 30 in the spotter base. The pins abut against the vertical face of the step in the spotter base, thus positioning the apertures in the wicking plate over the opening in the U-shaped cut-out. In this position the wicks 44 (one of which is shown in FIGS. 7 and 8) can be loaded into the wells 38 in the wicking plate 36, the wick stems 46 protruding through the base of the plate 36 into the void created by the U-shaped cut-out 30.

In its reversed position, i.e., with the pins facing away from the base 10, its long edge 56 engages the step 24 and positions the wicking plate with its wells directly over the solvent trough 28.

Wicks—The wicks 44 (FIGS. 7 and 8), molded from suitable porous plastic, such as polyethylene, with stems 46 and dome-shaped top 48, replace the capillary pipet, plumbing and auxiliary sample reservoir of the prior art capillary spotting device.

In the analysis of drugs of abuse, once the materials of interest have been extracted from the biological sample they are evaporated to dryness in a glass vessel and then resolubilized in an organic solvent, 20 to 50 $\mu l$ in volume, which is also used to wash down the sides of the vessel to collect all of the sample. With the capillary system, these liquid samples will either have to be applied directly to the plate, in increments of 1 to 2 $\mu l$ at a time by hand spotting, or transferred to a sample reservoir in a spotting device where in increments, or continuously through a plumbing arrangement, the samples are applied by a series of capillary pipets to the TLC plate.

With the wick system of the invention all that is needed, once the sample has been resolubilized, is to drop the wick into the liquid sample which is then absorbed by the wick and left to dry in the evaporation vessel. The wick is thus its own reservoir and as the sample is allowed to dry in the wick, a liquid sample, considerably larger than the fluid absorption capacity of the wick itself, can easily be accommodated.

Once the wicks are dry, they are placed in the wells or apertures 38 in the wicking plate 36. Here the sample, contained throughout the entire body of the wick 44 can either be concentrated in the upper portion of the wick, by touching the base of the wick stems to a strip of absorbent material saturated with a suitable solvent, or the plate and wicks can be placed directly into position over the solvent trough 28 in the spotter base 12 and the samples flushed out of the wicks, by the solvent in the trough, directly onto the adsorbent surface of the TLC plate. In this latter performance aspect the novel spotter exceeded its expected capability in that it would be expected that any sample in the wick stem would be leached out into the transfer solvent in the trough, when the stem was immersed into that solvent, and result in a possible transfer of this leached sample into neighboring wicks. In practice, particularly when a strong transfer solvent was used, this did not happen, even when the samples used contained 5 to 10 times as much sample material as is normally encountered in drug analysis.

The actual sample transfer is accomplished by the capillary, wicking action, of the fine open pore structure of the wick itself. Thus the wick in effect supplies its own plumbing.

As mentioned, the wick itself 44 is designed with a dome-shaped, hemispherical top 48 which provides a fine limited area of contact with the adsorbent surface 50 of the TLC plate 16 (tangential contact of a sphere with a plane surface). However, due to the blunt nature of the dome shape and the soft composition of the porous polyethylene, the wick will not damage the adsorbent surface of the TLC plate even if relatively large amounts of pressure are brought to bear at the area of contact. Whereas, with the hard, small diameter, glass micro capillary pipets, the adsorbent surface of the TLC plate can be easily damaged during the spotting operation. The design and nature of the material composition of the wick avoid this problem.

OPERATION OF THE DEVICE

The spotter base 10 is placed on a flat, level surface. The wicking plate 36 is then laid in the recessed, stepped area so that the wicks may be loaded from the top into the apertures 38 and the positioning pins 40 abut against the vertical face of the step 24, serving as stops properly to locate the plate. The ends of the wicking plate rest on the surfaces 52, 54 of the extensions 32 and 34.

The dried, sample-loaded wicks 44 are then removed from the evaporation vessels and loaded into the wells 38 in the wicking plate 36. Once all of the wicks are loaded in the wells, a glass plate (TLC plate), spare wicking plate or any other clean, flat-surfaced plate is laid across the tops of the wicks and pressed gently but firmly down to seat the wicks uniformly in their wells.

Following this, a solvent saturated absorbent strip of material, such as Bench-Kote, can be inserted into the U-shaped cut-out area 30 beneath the wick stems 46 and brought into contact with them to preconcentrate all of the sample in the top portion of the wick. This step is particularly useful if a weak transfer solvent is selected for the spotting operation.

The solvent well is filled to a few mm of its brim with the transfer solvent.

The wicking plate 36 is removed from the recessed step area, reversed 180° so that its long, non-pin-containing, edge 56 faces the vertical face of the step 24. The plate is laid back down in the recess so that the unpinned edge 56 abuts against the vertical face of the step 24 and the wick stems 46 are immersed in the transfer solvent in the trough 28.

A TLC plate 16 is then inserted into the spotter base 10, adsorbent side down, at an angle (approximately 30° to 40°), so that the leading edge 58 of the plate rests against the base of the back guide rail 14 and can pivot against it. The plate is now spotted with the sample by swinging it down into contact with the wick tips 48.

If a strong transfer solvent is used, i.e., one in which the sample would exhibit appreciable mobility on the particular adsorbent if it were used to chromatographically develop the plate, the plate should only make a short momentary contact with the wicks before beomg swung up and away from the wicks and the spotted samples dried with a hand-held hair dryer. This operation is repeated two or three more times to assure that all of the sample has been transferred from the wick to the plate.

On the other hand, if a weak transfer solvent is used, i.e., one in which the sample would exhibit little or no mobility on that adsorbent if it were used to chromatographically develop the plate, the plate should rest in contact with the wicks until the spreading rings of transfer solvent start to touch one another. At this point the plate is swung away from the wicks and the plate is dried with a hand-held hair dryer. This operation is repeated two or three more times to assure that all of the sample has been transferred from the wick plate.

The strong solvent transfer technique is best employed where maximum speed of operation is desired or for spotting a sample onto a weakly adsorbent material such as cellulose and Kieselgur. It does demand a quick reaction time and a certain amount of training to spot samples in this manner, in small compact areas without any significant circular predevelopment.

The weak solvent transfer technique is best employed where minimal training, simplicity and ease of operation are desired and where one is spotting on strong adsorbents such as alumina and silica gel. The technique is based on the fact that while the polyethylene wicks are excellent absorbents, they are very weak adsorbents. As such, while a sample may exhibit very little or no apparent mobility on a strong adsorbent with a particular transfer solvent, that same sample may have an appreciable mobility, under the influence of that same solvent, in the weakly adsorbent wick. As such, an appreciable volume of that weak solvent may be used to completely flush a sample from a wick, onto a TLC plate, where the sample will be immobilized by the strong adsorbent at the point of contact of the wick with the plate. Thus the sample is automatically confined to a small, uniform and compact area on the surface of the plate, while the transfer solvent continues to flow outward from the point of wick contact onto the surface of the plate in an ever-widening circle. When the spotting operation is completed, the plate is dried and ready to be chromatographically developed.

While we have disclosed and described a presently preferred mode for carrying out our invention, it will be understood that such is not by way of limitation. It is intended that the scope of the invention be limited only by the proper scope to be afforded the appended claims.

We claim:

1. A device for spotting samples at spaced locations on the adsorbent surface of a TLC plate comprising a base member having an elevated flat TLC plate-supporting portion extending forwardly from its back and a stepped-down portion at its front containing a solvent trough and a wicking plate containing wick-receiving apertures adapted to be positioned on said stepped-down portion with said apertures over said trough so that the lower ends of wicks held in said apertures will dip in said trough, said stepped-down portion and said wicking plate being so disposed and arranged that a TLC plate positioned on said elevated portion will overhang said wicking plate so as to engage and be spotted by the upper ends of said wicks.

2. A device as claimed in claim 1 wherein said base member is provided with guides adjacent said elevated and stepped down portions to aid in positioning said TLC plate.

3. A device as claimed in claim 1 or claim 2 wherein said base is provided with a pair of spaced extensions from one of its edges adapted temporarily to support said wicking plate when wicks are being loaded into said apertures.

4. A device as claimed in claim 3 where said spaced extensions extend forwardly from said base to define a U-shaped cut-out therein adjacent said stepped-down trough-containing portion.

5. A device as claimed in claim 1 or claim 2 including an abutment between said elevated portion and said stepped-down portion adapted to cooperate with said wicking plate so as to position it over said trough with the lower ends of its wicks dipped therein.

6. A device as claimed in claim 5 wherein said wicking plate is provided with spacing means along one edge adapted to engage said abutment to aid in positioning said wicking plate with its apertures over said U-shaped cut-out, the other edge of said wicking plate being adapted to engage said abutment when the wicking plate is reversed to aid in positioning it with its apertures over said trough.

7. A device as claimed in claim 2 wherein said base member is unitary and formed from solvent-resistant plastic and said guides comprise upstanding rails on the back and two sides thereof.

8. A device as claimed in claim 6 wherein said spacing means comprises spaced pins extending outwardly from one edge of said wicking plate.

9. A method of spotting samples at spaced locations on a TLC plate which comprises
   allowing each sample in liquid solution to be absorbed by a porous wick,
   drying the wick,
   inserting the dried wick in an aperture in a wicking plate with its upper end protruding above the upper surface of the plate and its lower end depending beneath the bottom surface of the plate,
   contacting the lower end of the wick with a suitable solvent to concentrate the sample in the upper end of the wick, and,
   bringing such upper end into contact with the adsorbent surface of the TLC plate to spot the sample on such surface.

10. The method according to claim 9 wherein the sample is concentrated in the upper end of the wick by dipping the lower end in the solvent.

11. The method according to claim 9 wherein the sample is concentrated in the upper end of the wick by touching the base of the wick stem with a strip of absorbent material saturated with the solvent.

* * * * *

UNITED STATES PATENT AND TRADEMARK OFFICE
CERTIFICATE OF CORRECTION

PATENT NO. : 4,272,381

DATED : June 9, 1981

INVENTOR(S) : Richard D. Kremer and Michael J. Siebengartner

It is certified that error appears in the above-identified patent and that said Letters Patent are hereby corrected as shown below:

Col. 5, line 44, "beomg" should be --being--.

Col. 5, line 59, "wick plate" should be --wick to the plate--.

Signed and Sealed this

Twenty-fifth Day of August 1981

[SEAL]

Attest:

Attesting Officer

GERALD J. MOSSINGHOFF

Commissioner of Patents and Trademarks